United States Patent [19]

Rumberger et al.

[11] Patent Number: 5,030,213
[45] Date of Patent: Jul. 9, 1991

[54] CATHETER ROUTER AND METHOD OF USE

[76] Inventors: William E. Rumberger, 3523 Horton Rd., Newtown Square, Pa. 19073; Austin L. Hallman, 333 Riverview Rd., Swarthmore, Pa. 19081

[21] Appl. No.: 396,428

[22] Filed: Aug. 21, 1989

[51] Int. Cl.$^5$ ............................................. A61M 25/00
[52] U.S. Cl. .................................. 604/267; 15/104.09
[58] Field of Search ......................... 604/108, 266–268; 15/104.09, 104.01 R, 104.33

[56] References Cited

U.S. PATENT DOCUMENTS

| | | | |
|---|---|---|---|
| 958,854 | 5/1910 | Bunn | 604/267 |
| 1,485,298 | 2/1924 | Schroyer | 604/267 X |
| 1,522,368 | 1/1925 | Hoke | 15/104.09 X |
| 1,588,737 | 6/1926 | Hurd | 15/104.33 |
| 1,767,073 | 6/1930 | Ingold | 604/179 |
| 2,525,329 | 10/1950 | Wyzenbeek | 604/267 |
| 3,416,532 | 12/1968 | Grossman | 604/267 |
| 3,709,211 | 1/1973 | Hawkins | 128/760 |
| 3,732,858 | 5/1973 | Banko | 604/267 X |
| 4,228,802 | 10/1980 | Trott | 604/105 |
| 4,445,509 | 5/1984 | Auth | 604/266 X |
| 4,671,795 | 6/1987 | Mulchin | 604/281 |

Primary Examiner—John D. Yasko
Assistant Examiner—Adam J. Cermaki
Attorney, Agent, or Firm—Eckert Seamans Cherin & Mellott

[57] ABSTRACT

A catheter router assembly is disclosed for clearing salt blockages in a previously inserted catheter. A length of flexible, stainless steel cable is provided and a silver solder tip applied at the proximal end of the cable. The silver solder tip is then machined to form a suitable cutting edge for cutting or drilling through the body salts which clog the catheter. A pin vise is secured along the length of the flexible power cable to facilitate insertion of the cable into the catheter and to provide hand rotative power to the cutting tip sufficient to cut through the blocking salts and to clear the catheter for further use. The pin vise may be readily moved along the length of the power cable as necessary to define sufficient free, unsupported forward portions of the cable to reach and clear the blockage throughout the entire length of the catheter.

15 Claims, 1 Drawing Sheet

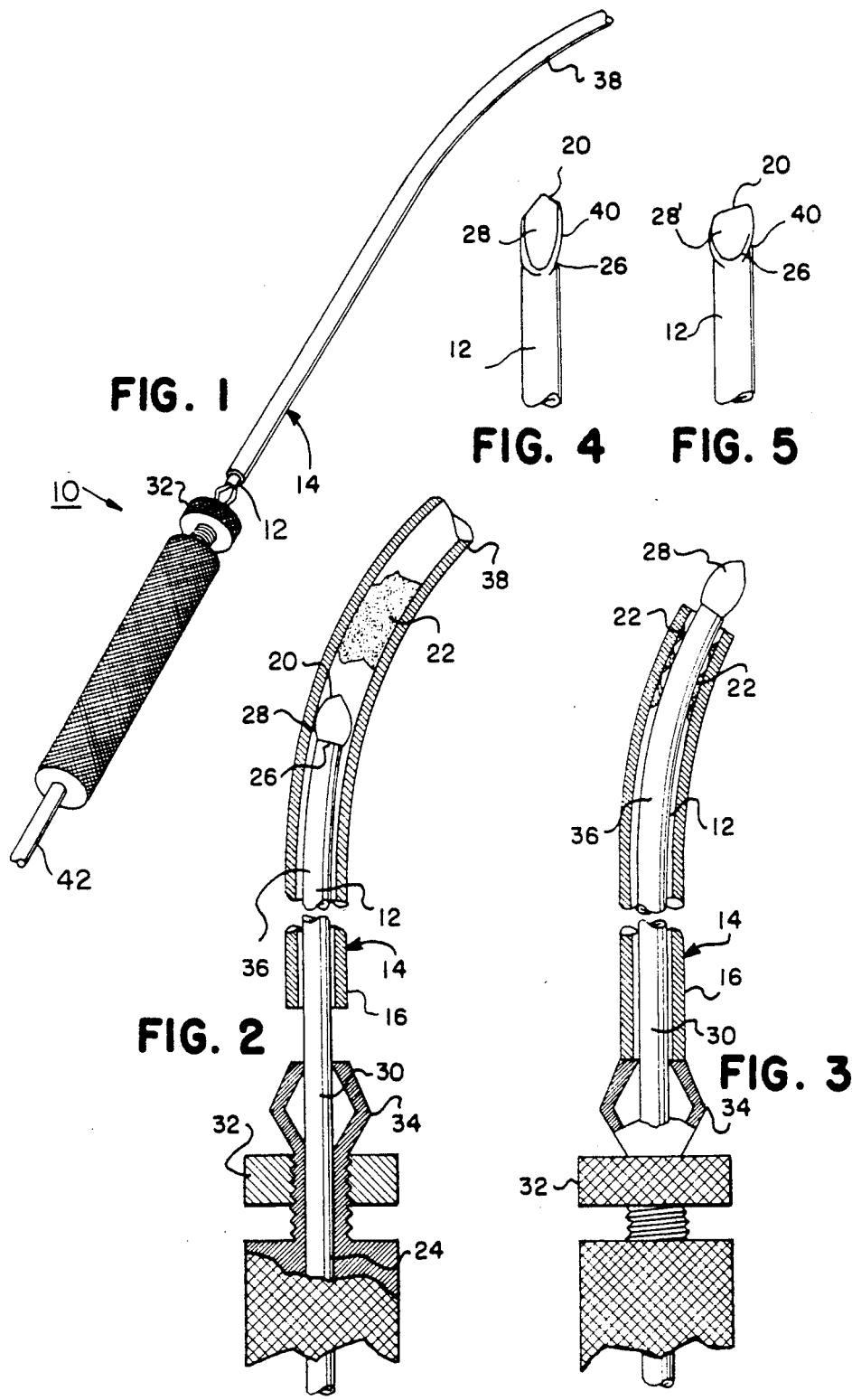

CATHETER ROUTER AND METHOD OF USE

BACKGROUND OF THE INVENTION

1. Field of the Invention

The present invention relates generally to the field of permanent and retrievable catheters, and more particularly, is directed to an insertable, flexible router suitable to clear blockages in a catheter without requiring physical removal of the catheter from the patient and to the method of using the catheter line router.

2. Discussion of the Prior Art

Catheters and other types of drainage tubes have long been utilized by surgeons and physicians in special applications for draining certain body fluids. In the case of kidney disease, it is now the common practice to insert a retrievable, flexible catheter having its proximal end positioned within a patient. The distal end of the catheter extends exteriorly of the patient's body in usual manner for drainage purposes. One such device is disclosed in U.S. Pat. No. 4,671,795 entitled "Permanent-/Retrievable Ureteral Catheter".

While such prior art devices are generally satisfactory when in use, experience has shown that the entrance to the inserted proximal end of the catheter has a tendency to become blocked with body salts during use, thereby requiring periodic cleaning by utilizing some type of suitable instrument. In those instances where the blockage cannot be relieved from exterior of the body, then it is necessary to surgically or otherwise remove the catheter for cleaning and repositioning within the body of the patient. This of course results in increased patient discomfort and in increased overall treatment costs and in increased risk of tissue damage or rupture of the ureter or of the aorta.

In an effort to provide some type of suitable cleaning implement for hollow conduits, such as catheters, which may be inserted in the human body, prior workers in the art have developed various types of tools and implements in an effort to unclog the conduit from exteriorly of the body to thereby allow continued use of the catheter. For example, in U.S. Pat. No. 958,854, there is disclosed hollow body or conduit that is particularly designed for and is suitable for insertion into a part of the body. A scraper is movable within the conduit and is endwardly provided with a cage which is utilized to prevent clogging. This device is intended for use with a rigid straight tube and is designed to penetrate soft tissue to provide a passageway for air or fluid to the outside of the body.

In U.S. Pat. No. 1,767,073, there is disclosed a catheter which comprises a tube having a head including a plurality of apertures. A cleaning wire including an exterior handle and a bent interior end is designed to be inserted into the tube to break encrustations from the inner wall of the tube. This device also comprises a straight rigid metal tube having no flexibility.

In U.S. Pat. No. 2,525,329, there is disclosed a trocar apparatus including a rigid straight tube which is designed to penetrate soft tissue and to provide a passageway for air or fluid from the penetrated area to outside of the body.

In U.S. Pat. No. 3,416,532, there is disclosed a drainage tube having an independent interior tube which is designed to assist in drainage by introducing a sucking action in addition to and in combination with a scraping action. There is no type of cutting or drilling feature present in conjunction with the interior tube.

In U.S. Pat. No. 3,709,211, a diagnostic myelography needle is disclosed for injecting and removing fluid material from channels of the human body, particularly the spinal canal. This device includes a hollow shank and an interior rod wherein the lower end of the rod is formed into a loop and the upper end of the rod is secured to a plug. This patent describes a rigid tube along with a stiff rod to aid in the aspiration of fluids and is not designed to clear encrustations or salts from a flexible catheter.

U.S. Pat. No. 4,228,802 discloses a multi-piece catheter which incorporates an auger for the removal of blood clots and debris which may cause blockage of the catheter. The device shows no means for boring or drilling through a blockage caused by encrustations of salts for subsequent drainage through the catheter without removal.

Accordingly, the need remains to provide an easily operable, flexible means for boring or drilling encrustations or salts which may form on and block the proximal end of a catheter from the exterior of the body and without requiring removal of the catheter.

SUMMARY OF THE INVENTION

The present invention relates to the field of medical devices in general, and more particularly, relates to an elongate, flexible boring or drilling member which is insertable through the distal end of an implanted catheter from exterior of the body to clear blockages at the proximal end of a catheter implanted within the body.

The catheter router of the present invention comprises a length of thin, strong, flexible cable suitable for removable insertion within a previously implanted catheter. The end of the flexible cable is modified to form a drill tip by brazing or soldering the cable end with silver solder or other suitable material and then machining the treated end to provide a suitable cutting tip. The cutting tip functions to dislodge the salts or other incrustation which form in the proximal end of the catheter by a scraping or drilling action. The dislodged salts can then pass over and about the formed cutting end and down along the outer periphery of the flexible routing cable for discharge through the catheter proximal end.

The routing cable can be rotatively powered by hand power, for example, by employing a pin vise, or optionally, it can be automatically powered by a suitable, small, properly connected electrical motor. The pin vise or motor, if a motor is employed, is designed to be readily movable along the length of the flexible power cable whereby the rotative device can be secured to the cable at increased distances from the cutting tip as the flexible cable is fed through the catheter and as portions of the materials causing the blockage are subsequently drilled and removed.

It is therefore an object of the present invention to provide an improved, flexible catheter router of the type set forth and the method of using the catheter router.

It is another object of the present invention to provide a novel catheter router which comprises a suitable length of thin, flexible steel cable having a proximal end and a distal end, the proximal end of the cable being ground or otherwise treated to form a cutting tip suitable for dislodging salts or other materials blocking the proximal end of a catheter and a cable rotative means releasably affixed to a portion of the cable exteriorly of the body to facilitate rotating the cutting tip and applying the cutting tip to the encrusted salts or other materials which form to cause catheter blockage.

It is another object of the present invention to provide a novel catheter router and method of use within a flexible conduit that has its proximal end blocked with encrusted salts wherein a flexible cable having a cutting tip ground on its proximal end is inserted into the flexible conduit until the cutting tip strikes the blockage material, rotatively working the flexible cable relative to the flexible conduit to remove portions of the encrusted materials, feeding the flexible cable further into the conduit and removing the remainder of the encrusted materials whereby the flexible conduit can be cleared from exteriorly of the body and without surgery.

It is another object of the present invention to provide a novel catheter router that is rugged in construction, simple in design and trouble-free when in use.

Other objects and a fuller understanding of the invention will be had by referring to the following description and claims of a preferred embodiment thereof, taken in conjunction with the accompanying drawings, wherein like reference characters refer to similar parts throughout the several views and in which:

BRIEF DESCRIPTION OF THE DRAWINGS

FIG. 1 is a perspective view showing the various parts of the catheter router in use in accordance with the teachings of the present invention.

FIG. 2 is an enlarged, partial elevation view of the catheter router in use in a first position and partially broken away to expose interior construction details.

FIG. 3 is an enlarged view similar to FIG. 2 showing the catheter router in a second position.

FIG. 4 is an enlarged, partial elevational view of the power cable end showing a first embodiment of a routing tip.

FIG. 5 is an enlarged view similar to FIG. 4 showing a second embodiment of a routing tip.

DESCRIPTION OF THE PREFERRED EMBODIMENT OF THE INVENTION

Although specific terms are used in the following description for the sake of clarity, these terms are intended to refer only to the particular structure of the invention selected for illustration in the drawings, and are not intended to define or limit the scope of the invention.

Referring now to the drawings, there is shown in FIG. 1 a catheter router assembly 10 which comprises generally a length of thin, flexible stainless steel cable 12 and means 32 to slowly rotate the cable. The flexible cable is designed and intended to permit a surgeon or other skilled person to effect the clearing of a salt blockage which may form in a previously inserted catheter 14.

The flexible cable 12 comprises a length of conventional stainless steel power cable of preferably 0.050 inches diameter and may be similar to small diameter, stranded, flexible power cable as manufactured and sold by S. S. White Industrial Products, Piscataway, N.J. 08854. Catheters presently most popularly employed as retrievable ureteral catheters, as described in U.S. Pat. No. 4,671,795 are generally constructed with a flexible, elongate body which is coiled at its proximal end to define a circular bend or pigtail. The flexible cable must be strong enough and stiff enough to uncurl the pigtail of the previously inserted catheter during the salt dislodging procedure.

The flexible stainless steel cable 12 of the present invention is modified at each end, in known manner, such as by brazing or by soldering with silver solder or other suitable material. The brazing or soldering at the distal end 24 of the power cable 12 is provided to form a closed end 42 to prevent unintentional unraveling of the strands which comprise the flexible cable 12. The silver solder at the proximal end 20 of the power cable 12 is applied and configured to form a slightly enlarged terminus 26. The terminus 26 serves the dual purposes of setting the end of the power cable to permanently prevent unraveling of the strands at the proximal end 20 and also to provide a suitable base material for forming a cutting tip 28 as hereinafter more fully described. The silver solder or brazed terminus 26 is formed smaller than the interior diameter of the catheter 14 and slightly larger than diameter than that of the power cable 12 itself to prevent the actual cutting/grinding edges of the cutting tip from cutting into the catheter wall especially where the pigtail portion of the catheter is entered by the cutting tip. This feature is especially critical where a "chisel-like" end is used as a cutting tip. Here the cutting tip is chamfered on its edges to assure protection of the catheter wall. The bulb portion of the tip is grooved or fluted to permit the dislodged salts to pass down toward the distal end of the catheter.

Referring now to FIGS. 4 and 5, the treated proximal end 20 of the power cable 12 is illustrated wherein the proximal end permanently closed by applying a silver solder or other suitable material terminus 26 of diameter slightly larger than the diameter of the flexible cable 12 itself. Once the silver solder or other suitable material has been properly applied and permanently affixed to the cable construction in well known manner, the silver solder or other material can then be machined or otherwise treated in known manner to form a cutting tip 28, 28', much in the manner of machining a conventional drill bit. Each type of cutting tip 28, 28' is particularly designed, shaped and formed to dislodge any salts 22 which may accumulate in the catheter whereby a drilling or scraping action upon rotation of the cutting tip 28, 28' relative to the catheter 14 can be achieved. This drilling or rotative action of the cable 12 facilitates and causes the cutting tip 28, 28' to cut through the accumulated salts 22 and thereby succeeds in dislodging such salts. Such encrustation or accumulated salts would otherwise be quite unaffected by the prior art blunt instruments, which instruments could only be rammed or pressed against the salts 22, rather than be rotated to actually cut through the blockage material. Preferably, the catheter router end 20 is longitudinally undercut to provide fluting or grooves 40 to facilitate movement of the dislodged salts past the cutting tip 28, 28' toward the distal end of the catheter 14.

The routing or power cable 12 can be rotatively powered, preferably by hand, by employing a conventional pin vise 32 of the type having an easily adjustable chuck 34 to alternately secure and release the power cable 12 for functioning of the power cable to clear the catheter blockage in the manner hereinafter more fully set forth. The pin vise 32 may be of a type suitable for use with thin, flexible stainless steel cable such as the pin vise currently manufactured and sold by Starett Manufacturing Company, Athol, Mass. 01331.

As shown, the flexible cable 12 is fed through the pin vise and through the chuck 34 so that the pin vise 32 can be readily affixed to the body 30 of the cable 12 to facilitate rotative use of the router assembly 10 as hereinafter set forth or the pin vise can be moved along the body of the cable for easy length adjustment purposes.

In order to use the catheter line router assembly 10 of the present invention to clear a blockage in a previously inserted catheter 14, the pin vise 32 is moved relative to the body 30 of the power cable 12 to define a free, unsupported, forward portion 36 of the flexible, cable 12 of length sufficient to reach the blockage 22 in the catheter 14. The pin vise chuck 34 can then be tightened about the cable 12 in the usual manner to initially define a first length of free forward portion 36 of the cable 12. The vise defined free end portion 36 of the power cable 12 is then inserted through the distal end 38 of the catheter 14 and is urged through the catheter body 16 until the flexible cable cutting tip 28 reaches and stops against the accumulated salt blockage 22. Using the pin vise to apply a turning action, the power cable cutting tip 28 can then be rotated by the fingers (not shown) of the surgeon or other operator (also not shown) to provide a drilling action sufficient to cut or drill through and dislodge the accumulated salts.

The cutting tip 28 of the flexible cable 12 may similarly be rotated by an accessory electric motor (not shown) should such an electric motor be employed in the operation in similar manner. Should such a motor be utilized, it should similarly be equipped with a cable clamping chuck to permit the cable free end portion 36 to be readily varied as the blockage clearing procedure progresses. Preferably, a fluoroscope is used in conjunction with the drilling operation so that the depth or length of penetration of the cutting tip 28 and its relation to the forward portions of the catheter 14 and to body tissues can be observed by the surgeon during the operation.

As the proximal end 20 of the power cable 12 proceeds into the blocked portion of the catheter 14, the pin vise chuck 34 can be released and moved further away from the proximal end 20 to define increased lengths of free cable portions 36 to permit the advance of additional lengths of the cable 12 into the blocked catheter 14. This process can be repeated as often as necessary until the cutting tip 28 cuts entirely through the blocked area and exits the proximal end 38 of the catheter 14. Once the blockage has been cleared, the flow of body fluids through the catheter will then resume in the normal manner. The catheter line router assembly 10 can be easily removed simply by pulling the power cable forward portion 36 outwardly of the catheter 14. The entire operation can be repeated as often as may be necessary with complete safety and with as little inconvenience to the patient as possible.

Although the invention has been described with a certain degree of particularity, it is understood that the present disclosure has been made only by way of example and that numerous changes in the details of construction and the combination and arrangement of parts may be resorted to without departing from the spirit and scope of the invention. Thus, the scope of the invention should be not limited by the foregoing specification, but rather, only by the scope of the claims appended hereto.

We claim:

1. A catheter router assembly for clearing blockage in a previously inserted catheter comprising:
   a length of flexible cable diameter suitable to enter into and to slide within the said catheter, the cable comprising a body which terminates in a proximal end wherein a soldered terminus having a diameter is formed in the proximal end;
   a cutting tip formed in the soldered terminus, the cutting tip being adapted to be rotated to cut through and to clear blockages which may form in the catheter; and
   means affixed to the flexible cable to rotate the flexible cable within the catheter to cause the cutting tip to cut through the blockage.

2. The catheter router assembly 1 wherein the cutting tip is provided with grooves.

3. The catheter router assembly of claim 1 wherein the cutting tip is sufficiently chamfered on its edges to prevent cutting of the catheter wall.

4. A catheter router assembly for clearing blockages in a previously inserted catheter comprising:
   a length of flexible cable of diameter suitable to enter into and to slide within the said catheter, the cable comprising a body which terminates in a proximal end;
   a cutting tip formed in the proximal end of the power cable, the cutting tip being adapted to be rotated to cut through and to clear blockages which may form in the catheter; and
   means affixed to the flexible cable to rotate the flexible cable within the catheter to cause the cutting tip to cut through the blockage the means to rotate comprising a vise.

5. The catheter router assembly of claim 4 wherein the vise comprises a chuck and means to alternately clamp the vise to the cable and to unclamp the vise from the cable.

6. The catheter router assembly of claim 4 wherein the vise comprises a central opening and wherein a portion of the flexible cable is positioned within the central opening.

7. The method of clearing an obstruction in a previously inserted catheter of the type having an interior conduit comprising the steps of
   forming a cutting tip in one end of a length of thin, flexible power cable;
   inserting the one end of the power cable into the catheter and applying the cutting tip against the obstruction;
   rotating the cutting tip relative to the obstruction; and cutting through the obstruction with the cutting tip to clear the continuous interior conduit through the catheter.

8. The method of claim 7 wherein the rotating comprises applying the vise over a portion of the power cable exteriorly of the catheter and clamping the vise to the power cable in a first position to define a first length of free, unsupported, forward portion of the flexible power cable.

9. The method of claim 8 wherein the inserting comprises inserting the said free unsupported forward portion of the flexible power cable into the catheter.

10. The method of claim 9 and the further step of applying the cutting tip against the obstruction by hand power at the vise.

11. The method of claim 10 wherein the rotating the cutting tip is by manual turning of the vise.

12. The method of claim 8 including the further step of releasing the vise from association with the power cable, moving the vise further from the said cutting tip and reclamping the vise to the flexible power cable to define an increased length of free, unsupported forward cable portion.

13. The method of claim 12 comprising the further step of inserting the increased length of free, unsupported forward portion of the cable into the catheter by hand power at the vise until stopped by the obstruction.

14. The method of claim 13 comprising the further step of rotating the vise and the cutting tip by hand until the obstruction is cleared.

15. The method of claim 13 wherein the catheter is formed with a curled pigtail and the further step of uncurling the pigtail with the free, unsupported forward portion of the cable.

* * * * *